United States Patent [19]

Orsing

[11] 4,074,435
[45] Feb. 21, 1978

[54] DISPOSABLE SALIVA EJECTOR

[76] Inventor: John Harry Orsing, Avangsgatan 2, S-253 71 Helsingborg, Sweden

[21] Appl. No.: 687,134

[22] Filed: May 17, 1976

[30] Foreign Application Priority Data

May 20, 1975 Sweden .................................. 7505700
Mar. 10, 1976 Sweden .................................. 7603150

[51] Int. Cl.² ............................................. A61C 17/04
[52] U.S. Cl. ....................................................... 32/33
[58] Field of Search ............................. 128/276; 32/33

[56] References Cited

U.S. PATENT DOCUMENTS

| 950,109 | 2/1910 | Levkowicz | 32/33 |
| 2,529,499 | 11/1950 | Jankelson | 32/33 |
| 3,395,705 | 8/1968 | Hamilton | 128/276 |
| 3,541,583 | 11/1970 | Deuschle | 32/33 |
| 3,881,254 | 5/1975 | Epstein | 32/33 |

Primary Examiner—Robert Peshock

[57] ABSTRACT

A disposable saliva ejector has a tubular stem and a sleeve slid onto the inlet end thereof. A passage in the interface between the stem and the sleeve provides a restricted communication between the surrounding at the inner end of the sleeve and the interior of the stem.

5 Claims, 10 Drawing Figures

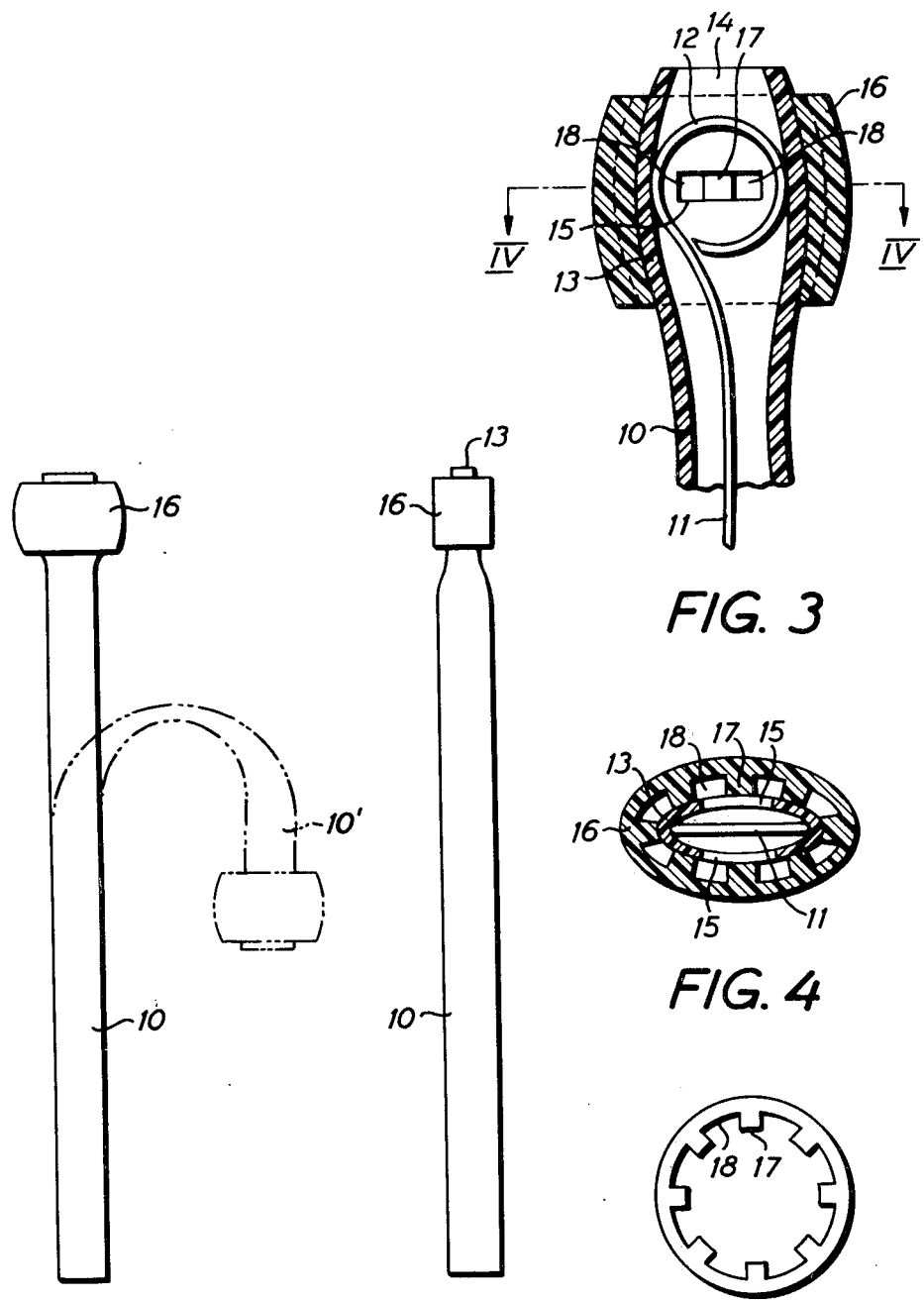

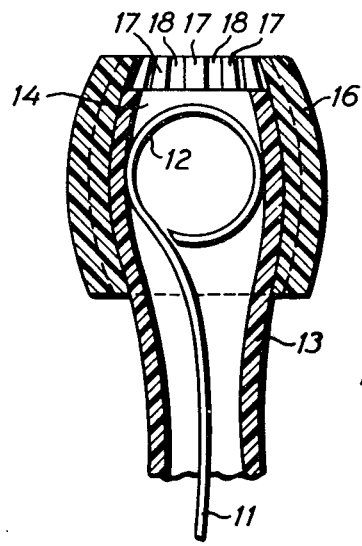
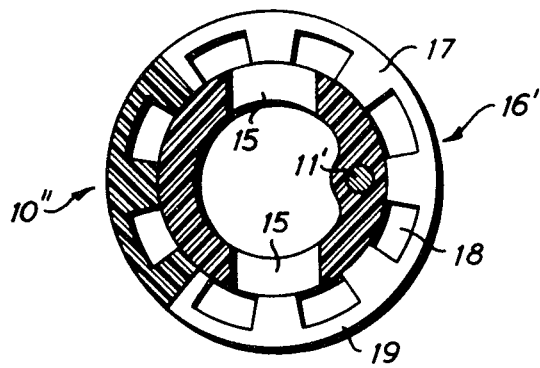
FIG. 6  FIG. 10
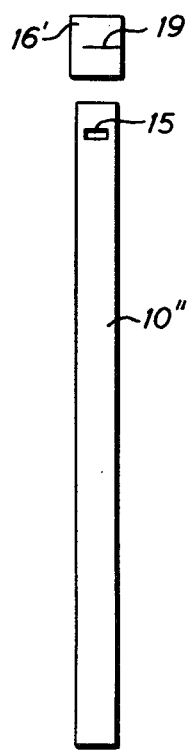
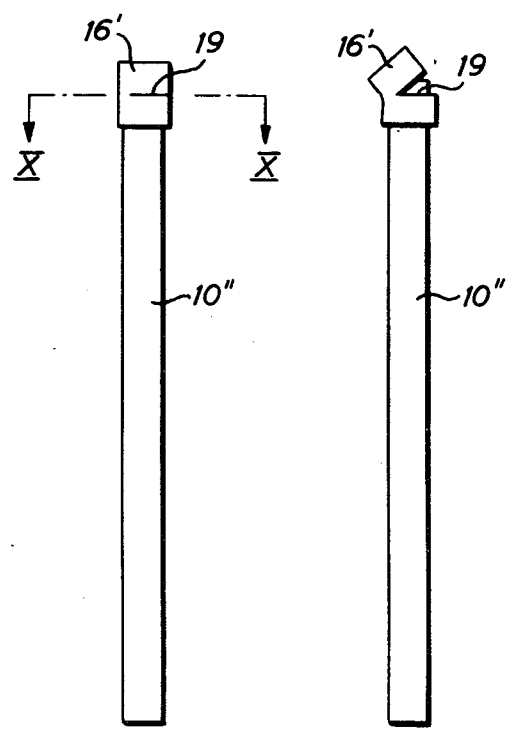
FIG. 7  FIG. 8  FIG. 9

4,074,435

DISPOSABLE SALIVA EJECTOR

BACKGROUND OF THE INVENTION

1. Field of the Invention

This invention relates to saliva ejectors which are used to drain the oral cavity when a dental or other operation is being performed therein. More particularly, this invention relates to a disposable saliva ejector, i.e., an ejector which is discarded after having been used once.

The disposable saliva ejector according to the invention is of the type comprising a tubular stem open at both ends thereof, one end of which forms a suction inlet opening when the other end thereof is connected to a suction tube.

2. Description of the Prior Art

When a saliva ejector is applied over the lower tooth ridge of the mouth for the withdrawing of saliva from the oral cavity the suction applied to the saliva ejector may draw local portions of the soft tissues of the oral cavity into the opening or openings provided in the suction inlet end of the saliva ejector if such tissues are contacted by the suction inlet end. Thereby, the passage to the interior of the tubular stem may be obstructed at said opening or openings causing unsatisfactory functioning of the ejector. Additionally, the tissue drawing may be painful to the patient and may cause discomfortable wounds in the mouth. Especially when the suction tube connects the ejector with a central suction device which produces high vacuum there is a great risk for the tissues being drawn into the ejector.

According to U.S. Pat. No. 2,529,499 to Jankelson, issued Nov. 15, 1950 the tissue drawing in a saliva ejector is eliminated or reduced by an inlet nozzle construction comprising several individual parts which are interconnected to form a system of openings and passages in the nozzle, which admits air to the interior of the ejector to limit the degree of suction in case the suction inlet opening or openings through which the saliva shall be drained from the oral cavity when the ejector is being used should be contacted and covered by tissues and thus obstructed. The arrangement provided for this purpose in the saliva ejector disclosed in the patent referred to is constructed and designed for a saliva ejector which is intended to be used several times and to be sterilized after each use. Due to the elaborate construction thereof it is not suited to be incorporated into a disposable saliva ejector which must be produced at a reasonably low cost.

SUMMARY OF THE INVENTION

It is a primary object of this invention to provide a new and improved disposable saliva ejector which shall be discarded after having been used once.

It is a further object of this invention to provide a new and improved disposable saliva ejector which eliminates the risk of tissue drawing and thus the functional drawbacks and the discomfort caused to the patient by such tissue drawing as described above.

A still further object of this invention is to provide a new and improved disposable saliva ejector which comprises a minimum of parts which can be readily and rapidly assembled by automatic operations.

Yet another object of this invention is to provide a new and disposable saliva ejector wherein the admission of air provided in order to avoid tissue drawing may be controlled in order to adjust the air admission to the power of the suction device connected to the ejector.

Additional objects and advantages of the invention will be set forth in part in the description which follows and in part will be obvious from the description, or may be learned by practice of the invention. The objects and advantages of the invention may be realized and attained by means of the instrumentalities and combinations particularly pointed out in the appended claims.

To achieve the foregoing objects and in accordance with the purpose of the invention, as embodied and broadly described herein, the disposable saliva ejector of this invention comprises a tubular stem open at both ends thereof one end of which forms a suction inlet opening when the other end thereof is connected to a suction tube, and a sleeve slid onto said one end of the tubular stem and covering part thereof, at least one passage being arranged between said tubular stem and said sleeve to connect the surrounding at the inner end of the sleeve with the interior of the tubular stem.

Preferably the sleeve projects beyond said one end of the tubular stem.

It is also preferred that the tubular stem forms at least one aperture in the side wall thereof covered by the sleeve and communicating with said passage.

It is also preferred that the inside surface of the sleeve is grooved and forms said passage together with a smooth outside surface of a tube forming the tubular stem.

It is also preferred that the sleeve forms a cut extending over at least half the circumference of the sleeve and that the sleeve is formed of a flexible material allowing the sleeve to be opened at the cut and the outer end portion of the sleeve to be turned off partially from the end of the tubular stem at the suction inlet end thereof.

The accompanying drawings, which are incorporated in and constitute a part of this specification, illustrate several embodiments of the invention and, together with the description, serve to explain the principles of the invention.

BRIEF DESCRIPTION OF THE DRAWINGS

Of the drawings:

FIG. 1 is a side view of a first embodiment of the saliva ejector according to the teachings of the invention;

FIG. 2 is a similar side view at right angle to that in FIG. 1;

FIG. 3 is an enlarged fragmentary axial sectional view of the saliva ejector shown in FIGS. 1 and 2 at the suction inlet end thereof;

FIG. 4 is a cross sectional view along line IV — IV in FIG. 3;

FIG. 5 is an enlarged end view of a hose grooved on the inside thereof, from which the sleeve arranged on the saliva ejector is made;

FIG. 6 is a view similar to that in FIG. 3 of a second embodiment of the saliva ejector according to the teachings of the invention;

FIG. 7 is a side view of a third embodiment of the saliva ejector according to the teachings of the invention the tubular stem and the sleeve being shown dissembled and separated from each other;

FIG. 8 is a side view of the saliva ejector shown in FIG. 7 in the assembled normal condition thereof;

FIG. 9 is a side view of the saliva ejector shown in FIGS. 7 and 8 adjusted for an increased admission of air; and FIG. 10 is an enlarged cross sectional view along line X — X in FIG. 8.

Reference will now be made in detail to the present preferred embodiments of the invention, examples of which are illustrated in the accompanying drawings.

DESCRIPTION OF THE PREFERRED EMBODIMENTS

Referring now to FIGS. 1 to 4 it is shown therein a first embodiment of the saliva ejector according to the teachings of the invention intended to be discarded after having been used once in order to avoid the time-consuming sterilization work which is necessary when the saliva ejector is intended to be used several times and accordingly has to be sterilized after each use.

The saliva ejector is of the type disclosed in U.S. Pat. No. 3,913,231 to Orsing, issued Oct. 21, 1975 and comprises a flexible tube 10 open at both ends thereof which may be made of a soft plastic material and may comprise a short length of conventional flexible polyethylene hose or tubing of circular cross sectional form. There is inserted into the tube a substantially plastically flexible wire 11, FIG. 3, such as an iron wire which is cadmium plated or protected against rust or other corrosion in any suitable way. According to the teachings in said patent wire 11 permits tube 10 to be bent to any suitable form and stiffens the tube so that it will maintain the form which has been imparted to it. The wire has a bend formed as a substantially circular closed loop 12 which is drawn completely into tube 10 from one end thereof. The loop has a largest cross dimension (diameter) that is larger than the inner cross dimension (diameter) of the tube and as a consequence thereof there is provided by drawing the loop into the tube a stretching and thus a flattening of the tube in the region of the loop so that the tube forms there a flat portion 13 the tube being contracted at axially opposite sides of the loop. Thus, the tube wall forms in the region of the loop a local symmetrical protrusion which follows the form of the loop. The loop and accordingly the wire as whole is thereby retained in the intended position in the tube.

At portion 13 tube 10 forms at the adjacent end thereof a narrow slot-like slightly elliptical suction inlet opening 14 because the tube is not at this end completely closed by the loop thanks to the fact that the flattened wall portions have a slightly curved form due to the inherent tendency of the tube to retain the round form thereof. Further suction inlet openings are arranged by the provision of two opposed rectangular apertures 15 in portion 13.

Thus it will be seen that tube 10 including wire 11 constitutes a tubular stem of the disposable saliva ejector described. One end of this stem, the upper end as seen in FIGS. 1 and 2, forms a saliva inlet when the other end, the lower end as seen in FIGS. 1 and 2, is connected to a suction hose or tube communicating with a dental suction device.

The ejector is delivered from the manufacturer in the form disclosed in solid lines in FIGS. 1 and 2, i.e., with a straight tubular stem, and is then bent by the dentist when it is to be used, to any suitable form adapted to the work to be performed in the oral cavity in the actual case. However, this form is usually the hook shaped form disclosed by dot-and-dash lines 10' in FIG. 1 so that the ejector may be applied over the lower tooth ridge of the mouth. Other forms are of course conceivable depending on the conditions in each individual case of use.

A sleeve 16 is slid onto the inlet suction end of the tubular stem and covers the stretched and flattened end portion 13 thereof. It is disposed inwardly of suction inlet opening 14. The sleeve comprises a piece of soft or flexible plastic hose or tubing such as a piece of polyethylene hose and of a length which is a small fraction of the length of tube 10. The sleeve follows the bulging form of portion 13 as shown in FIGS. 1 and 3. Such plastic hose could have the profile disclosed in FIG. 5 in the drawings. It will be seen that the profile shown therein comprises axially extending ribs 17 and grooves 18 therebetween on the inside surface of the hose. When sleeve 16 is positioned on the tubular stem 10, 11 in the manner described it covers the rectangular apertures 15 provided in the side wall of the tube 10 forming part of the tubular stem of the saliva ejector. However, ribs 17 form spacers between the outside surface of the tube and the sleeve and grooves 18 therebetween form passages in the interface of the tube and the sleeve to connect the surrounding at the inner end of the sleeve, i.e., the lower end in FIGS. 1 to 3, with the interior passage of the tubular stem through apertures 15 in the side wall of tube 10.

If suction is applied to the lower end of the saliva ejector described a suction action will be obtained at inlet suction opening 14 at the upper end of the ejector but air will also be admitted from the surrounding through the passages formed between the outside surface of tube 10 and the grooved inside surface of sleeve 16 from the inner end of the sleeve to the interior passage of the tube via apertures 15. The air admitted through passages 18 preferably should form a substantially lower air flow than that obtained through suction inlet opening 14 in order not to interfere with the intended use of the saliva ejector. The admission of air may be controlled by suitable dimensioning of the air passage through grooves 18 and apertures 15. This air flow may be termed a "false draught" since it does not positively contribute to the suction effect produced for the intended purpose of draining the oral cavity by means of the saliva ejector.

When the saliva ejector is being used usually in the form shown by dot-and-dash lines 10' in FIG. 1 and is applied over the lower tooth ridge of the mouth it is possible for the inlet suction opening 14 under circumstances to press or abut against the soft tissues of the oral cavity, opening 14 being closed thereby and possibly also the outer ends of grooves 18 in the inside surface of sleeve 16. The main drainage flow through the saliva ejector thereby will be interrupted. The tissue drawing otherwise araising in this situation is avoided in the saliva ejector described thanks to the "false draught" referred to above which avoids the risk for the tissues to be subject to a suction action which is strong to be painful to the patient or to produce mouth wounds in the oral cavity. When the saliva ejector is bent to the form 10' it is excluded that the inner ends of grooves 18 are obstructed by the tissues of the oral cavity, and also when the saliva ejector is bent to other forms than that shown by dot-and-dash lines in FIG. 1 it is excluded that sleeve 16 will be totally obstructed at both ends thereof. Thus, communication between the interior passage of tube 10 and the surrounding is always insured in order to provide a "false draught" when the saliva ejector described is being used.

According to FIGS. 1 to 3 sleeve 16 is spaced inwardly of suction inlet opening 14 but it may also be flush with said opening or even project a distance there-from without the intended functioning of the sleeve being affected thereby. The latter arrangement is shown in FIG. 6.

Referring now to FIG. 6 it will be seen that sleeve 16 projects a distance beyond the suction inlet opening 14 of tube 10. In this embodiment apertures 15 in the side wall of tube 10 may be provided as in the embodiment described with reference to FIGS. 1 to 5 but it is not necessary to provide such apertures and they are not provided in the embodiment of the invention shown in FIG. 6. In this case the outer end of sleeve 16 may be closed by the mouth tissues when the saliva ejector is being used but in that case the "false draught" as defined above will still be obtained although no apertures 15 are provided. Air will be admitted from the surrounding at the inner end of sleeve 16 through grooves 18 and the inlet end of tube 10 which is spaced from the adjacent end of sleeve 16.

The vacuum provided by dental suction devices may be of varying strength and it is well known that central suction devices, i.e., such devices which are servicing a plurality of dentists provide a vacuum which is much stronger than that provided by conventional suction devices servicing one or two dentists only. Therefore, it may be desirable to control in a simple way the "false draught" provided in the saliva ejector in order to adapt it to the vacuum provided by the suction device.

Referring to FIGS. 7 to 10 there is shown an embodiment of the present invention which allows such control to be performed.

The saliva ejector disclosed in FIGS. 7 to 10 comprises a flexible tube 10" which is made of a soft plastic material such as a length of flexible polyethylene hose or tube a substantially plastically flexible wire 11' such as an iron wire being embedded into the tube wall to stiffen tube 10" for the purpose described with reference to the embodiment shown in FIGS. 1 to 3. The tubular stem 10", 11' thus formed is of a construction which is well known in the art. Onto tubular stem 10", 11' there is slid a sleeve 16' which comprises a piece of flexible plastic hose or tube of the profile disclosed in FIG. 5 and described above providing ribs 17 and grooves 18 on the inside surface thereof. As in the embodiment according to FIGS. 1 to 3 it is preferred that there are provided in the portion of tube 10' covered by sleeve 16' two diametrically opposite rectangular apertures 15 although such apertures may be dispensed with. Sleeve 16' projects beyond the end of tube 10".

In sleeve 16' there is provided a cut 19 which may be formed as a narrow slot. However, it is preferred from a manufacturing point of view to provide a simple cut by means of a knife because the operation to be performed in that case can readily be incorporated in an automatic manufacturing process and leaves no scrap material. Cut 19 extends over at least half the circumference of sleeve 16' and preferably, as in the embodiment shown, over ¾ of the circumference of the sleeve as will be seen from FIG. 10.

Normally the sleeve operating to provide a "false draught" in the manner described above is in the condition disclosed in FIG. 8, i.e., cut 19 is closed and provides substantially no communication between the surrounding and the grooved inside surface of sleeve 16'. By separating the sleeve more or less at the cut by turning off the outer end portion of the sleeve partially from the tubular stem 10", 11' as shown in FIG. 9 the "false draught" at the sleeve will be increased further as may be required in order to prevent the saliva ejector from adhering to the tissues of the oral cavity due to the suction applied by the suction device to which the saliva ejector may be connected. An increased admission of air will be obtained through the opened cut of sleeve 16' to grooves 18 in addition to that maintained through the ends of the grooves at the inner end of the sleeve.

Modifications can be made in the embodiments described. Thus the outside surface of the tubular stem may be grooved and the inside surface of the sleeve slid onto the stem be smooth. The grooves and ribs on the sleeve or on the tubular stem, as the case is, need not necessarily be straight and extend axially. They may also extend helically and have a great pitch in each of the embodiments described above. The sleeve may be loose on the tubular stem but it may also be fixedly attached thereto for instance by ultrasonic welding. In case of the embodiment shown in FIGS. 7 to 10 only the inner part of the sleeve should be fixedly attached to the tubular stem so that the outer part of the sleeve can be turned off from the stem in the manner described.

The invention provides disposable saliva ejectors that may be easily assembled by automatic manufacturing methods and apparatus whereby it is possible to produce the saliva ejectors at a low cost. The invention also provides means to control in a simple manner the "false draught" as defined above on order to adapt the saliva ejectors to suction devices producing vacuum of varying strength.

It will be appratent to those skilled in the art that various other modifications and variations in addition to those mentioned above could be made in the saliva ejectors of the invention without departing from the scope and spirit of the invention.

I claim:

1. A disposable saliva ejector comprising a tubular stem open at both ends thereof, one open end of which being adapted to form a suction inlet opening through which saliva can be drawn by suction, and the other end thereof being adapted to be connected to a suction tube; and an external sleeve circumferentially disposed about said one end of the tubular stem and covering part thereof, defining with the exterior wall of the stem at least one passage therebetween; said sleeve having a cut extending over at least half the circumference thereof, and being formed of flexible material allowing the sleeve to be opened at the cut and the outer end portion of the sleeve to be turned away from the end of the tubular stem.

2. A disposable saliva ejector comprising a tubular stem open at both ends thereof, one open end of which being adapted to form a suction inlet opening through which saliva can be drawn by suction, and the other end thereof being adapted to be connected to a suction tube; and an external sleeve circumferentially disposed about said one end of the tubular stem and covering part thereof, defining with the exterior wall of the stem at least one passage therebetween; said sleeve projecting beyond said one end of the tubular stem, said tubular stem having at least one aperture in the side wall, covered by the sleeve and communicating with said passage, the inside surface of said sleeve being grooved to form said passage, said sleeve having a cut extending over at least half the circumference thereof, and being made of flexible material allowing the sleeve to be opened at the cut and the outer end portion of the sleeve to be turned away from the end of the tubular stem, whereby suction at the inlet opening is lessened to the extent that suction is drawn via the passage.

3. A disposable saliva ejector comprising a tubular stem including a flexible plastic tube open at both ends thereof, and a stiffening wire therein, one open end of said tubular stem being adapted to form a suction inlet opening through which saliva can be drawn by suction and the other end thereof being adapted to be connected to a suction line, and an external sleeve circumferentially disposed about said one end of the tubular stem, which covers part of the tubular stem and projects beyond said one end of the tubular stem, the inside surface of the sleeve being grooved and defining with the exterior wall of the stem at least one passage therebetween; and the side wall of the flexible plastic tube having at least one aperture in said portion covered by the sleeve to connect said passage with the interior of the tubular stem through said aperture, whereby suction at the inlet opening is lessened to the extent that suction is drawn via the passage.

4. A disposable saliva ejector comprising a tubular stem including a flexible plastic tube open at both ends thereof, and a stiffening wire therein, one open end of said tubular stem being adapted to form a suction inlet opening through which saliva can be drawn by suction and the other end thereof being adapted to be connected to a suction line, and an external sleeve circumferentially disposed about said one end of the tubular stem, which covers part of the tubular stem and projects beyond said one end of the tubular stem, the inside surface of the sleeve being grooved and defining with the exterior wall of the stem at least one passage therebetween; and the side wall of the flexible plastic tube forming at least one aperture in said portion covered by the sleeve to connect with the interior of the tubular stem through said aperture, said sleeve having a cut extending over at least half the circumference thereof and being made of flexible material allowing the sleeve to be opened at the cut and the outer portion to be turned away from the end of the tube; whereby suction at the inlet opening is lessened to the extent that suction is drawn via the passage.

5. A disposable saliva ejector as claimed in claim 4 in which said sleeve comprises a piece of flexible hose.

* * * * *